United States Patent
Magro et al.

(10) Patent No.: US 11,918,440 B1
(45) Date of Patent: Mar. 5, 2024

(54) ACTIVE ACOUSTIC AURAL DEVELOPMENT SYSTEM AND METHOD

(71) Applicant: Sonura, LLC, Philadelphia, PA (US)

(72) Inventors: Caroline Magro, Alexandria, VA (US); Tifara Boyce, Jamaica, NY (US); Sophie Ishiwari, Chicago, IL (US); Gabriela Cano, Lawrenceville, NJ (US); Gabriella Daltoso, Boise, ID (US)

(73) Assignee: Sonura, LLC, Philadelphia, PA (US)

( * ) Notice: Subject to any disclaimer, the term of this patent is extended or adjusted under 35 U.S.C. 154(b) by 0 days.

(21) Appl. No.: 18/206,904

(22) Filed: Jun. 7, 2023

(51) Int. Cl.
*A61F 11/14* (2006.01)

(52) U.S. Cl.
CPC ..... *A61F 11/145* (2022.01); *A61F 2250/0082* (2013.01)

(58) Field of Classification Search
CPC .. H04R 25/505; H04R 25/70; H04R 2225/41; G10K 2210/1081
USPC .................................................. 381/72, 312
See application file for complete search history.

(56) References Cited

U.S. PATENT DOCUMENTS

| | | | |
|---|---|---|---|
| 9,946,842 B1 * | 4/2018 | Stringham | G16H 80/00 |
| 10,413,696 B2 | 9/2019 | Kimock et al. | |
| 11,185,447 B2 | 11/2021 | Kimock et al. | |
| 2012/0215519 A1 * | 8/2012 | Park | H04R 3/005 381/17 |
| 2013/0133671 A1 * | 5/2013 | Fairclough | A61F 11/14 2/209 |
| 2013/0243227 A1 * | 9/2013 | Kinsbergen | H04M 1/6016 381/314 |
| 2019/0132691 A1 * | 5/2019 | Gehring | H04R 25/554 |
| 2020/0268260 A1 * | 8/2020 | Tran | A61B 5/1118 |
| 2021/0044883 A1 * | 2/2021 | Redfield | A61N 7/00 |
| 2021/0142880 A1 * | 5/2021 | Bangera | H04R 3/002 |
| 2021/0195732 A1 * | 6/2021 | Longinotti-Buitoni | H05K 3/361 |
| 2021/0205634 A1 * | 7/2021 | Sverdlov | G16H 10/60 |

OTHER PUBLICATIONS

Natus Medical Incorp., "Mini Muffs", www.mcarthurmedical.com.
Chouery et al., Use of Hearing Protection in Neonatal Intensive Care Unit Patients: A Systematic Review of the Evidence, JEHDI, 2018; 3(2):37-46.
Balsan et al., "A pilot study to assess the safety, efficacy and ease of use of a novel hearing protection device for hospitalized neonates", PMC, May 30, 2023, 19 pages.
Gallo, LM Figueroa et al., "Noise Pollution Control System in the Hospital Environment", J. of Physics: Conference Series 705 (2016) 1-10.

* cited by examiner

*Primary Examiner* — Alexander Krzystan
(74) *Attorney, Agent, or Firm* — Fish & Richardson P.C.

(57) ABSTRACT

Methods, systems, and apparatus, for a wearable aural development medical device and system. A medical device is worn by an infant while the infant is in a neonatal intensive care unit (NICU). In particular, the device protects the child's hearing by active filtering, while, at the same time, provides aural stimulation for development. In some implementations, a remote server system also enables people associated the child, e.g., parents and siblings, to provide recordings, such as recordings of their voices, for playback to the child.

20 Claims, 7 Drawing Sheets

ACTIVE ACOUSTIC AURAL DEVELOPMENT SYSTEM AND METHOD

BACKGROUND

This specification relates to medical devices and systems, and in particular to a medical device and system that provides active filtering hearing protection for an infant while also providing an aural development environment for the infant.

Approximately 500,000 births annually result in newborn admissions to Neonatal Intensive Care Units (NICUs) in the United States. Unfortunately, while providing life-saving treatments and therapies, NICUs expose newborns to high-frequency noises and levels for over twelve hours every day. At these levels and duration, such noises may potentially damage the newborns' hearing. In particular, monitors and alarms surrounding each crib emit a multitude of noises that may upset or startle the patients and contribute to a hazardous auditory environments for the patients. Such exposure has long-term consequences for "graduates," i.e., infants who have been discharged from the NICU. These children face an increased risk of hearing impairment and potential learning disabilities.

Additionally, this auditory environment often drowns out the sounds of human voices. This is detrimental to the child, because human voice has proven integral to the neurodevelopment of preterm newborns. The developmental impacts caused by a lack of early vocal contact is further exacerbated by the absence of interactions between patients/infants and their parents due to professional, personal, and financial burdens, and the inability of the parent to be in the NICU for extended periods of time. Quantitatively, the average time of parental visitation is less than one day each week, leading to fewer opportunities for newborns to hear the voices of their parents. This decrease in engagement has significant consequences for graduates, including impairment of linguistic development and impairment of the child-caregiver relationship during the first twenty-four months of these children's lives.

SUMMARY

The subject matter described in this document addresses the problem of providing hearing protection for infants while also provided an aural development environment that stimulates the infants' early stage neurological development.

In general, one innovative aspect of the subject matter described in this specification can be embodied in an aural developmental medical device that includes a first audio transducer device and a second audio transducer device that each transduce electrical signals into acoustic sounds; at least one microphone device that transduces received acoustic sounds into electrical input signals; electronics electrically coupled to the first audio transducer device, the second audio transducer device, and the at least one microphone device, wherein the electronics are operable to: associate the aural developmental medical device with an identifier, receive the electrical input signals from the at least one microphone device, electronically filter the electrical input signals to attenuate frequencies above a cutoff frequency that is at least octave above a fundamental frequency of a typical human voice to generate filtered electrical signals, provide the filtered electrical signals to the first audio transducer device and the second audio transducer device, generate, from audio data associated with the identifier and encoding a recording, recorded electrical signals, and provide the recorded electrical signals to the first audio transducer device and the second audio transducer device; and a flexible packaging that positions the first and second audio transducer devices relative to each other so that the first and second audio transducer devices can be respectively positioned over a left ear and a right ear of an infant.

Another innovative aspect of the subject matter described in this specification can be embodied in a system that includes one or more computer devices and instructions stored in a non-transitory computer readable medium that are executable by the one or more computer devices, and upon such execution cause the one or more computer devices to perform operations comprising: storing an association of patients and users, wherein the association establishes, for each patient: an aural developmental medical device issued to the patient and identified by a unique identifier, one or more users that are authorized to provide audio data for presentation on the aural developmental medical device issued to the patient, receiving, over a computer network and from a user device that is remote from the one or more computer devices and associated with a particular user, audio data encoding a recording, determining, based on the particular user, the particular patient associated with the particular user, storing, in the association for the particular patient, the audio data encoding the recording and received from the user device, and sending, to the aural developmental medical device issued to the particular patient, the audio data encoding the recording.

In general, one innovative aspect of the subject matter described in this specification can be embodied in a method that include the actions of storing an association of patients and users, wherein the association establishes, for each patient: an aural developmental medical device issued to the patient and identified by a unique identifier; one or more users that are authorized to provide audio data for presentation on the aural developmental medical device issued to the patient; receiving, over a computer network and from a user device that is remote from the one or more computer devices and associated with a particular user, audio data encoding a recording; determining, based on the particular user, the particular patient associated with the particular user; storing, in the association for the particular patient, the audio data encoding the recording and received from the user device; and sending, to the aural developmental medical device issued to the particular patient, the audio data encoding the recording.

Particular embodiments of the subject matter described in this specification can be implemented so as to realize one or more of the following advantages. The systems and methods described herein promote the cognitive development of newborns receiving NICU care by providing audio data for playback to the newborns, while also protecting them from the auditory hazards of their environments. In implementations that do not store the audio data locally, the systems and methods provide an extra layer of privacy protection as at the completion of care, the wearable medical device is disassociated with data stored remotely from the wearable medical device.

The wearable medical device can be inserted into an attachable pouch that is attached to headgear, e.g., a beanie, worn by the infant. In these implementations, the medical device may be easily removed from the pouch when the patient is discharged, thus allowing for easy sanitation and reuse of the wearable medical device.

The use of active filtering enables the pass thorough of human voices while actively suppressing noises outside of a normal human voice range, which, in turn, provides an advantage over passive hearing protection systems that also attenuate human voices. Remote access to a server system in data communication with the wearable medical device allows for family members to upload recordings for periodic playback to the patients, which stimulates neurological development and bonding while the child is receiving treatment in the NICU.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Overview

Figure 1:
FIG. 1 is an image of an infant wearing an aural development medical device.

As described above, the NICU environment is often a high-frequency and high-level noise environment. These noises may be unsettling to a newborn, and if loud enough, may also damage a newborn's hearing during prolonged exposure. One solution to protect a child's hearing is to simply provide passive hearing protection for the child, e.g., by use of ear muffs or by use of a sound-insulated incubator. However, this results in aural sensory deprivation, which can hinder the child's very early stage development.

The technology described in this written description relates to an aural developmental medical device and system. A medical device is worn by an infant while the infant is in a neonatal intensive care unit (NICU). In particular, the device protects the child's hearing while, at the same time, provides aural stimulation for development. In some implementations, a remote server system also enables people associated the child, e.g., parents and siblings, to provide recordings, such as recordings of their voices, for playback to the child.

The technology described in this written description solves the problem of aural sensory deprivation that occurs when protecting an infant's hearing, and thus does not inhibit the development that results from aural stimulation.

In one example implementation, an aural developmental medical device includes two audio transducers that are contained in flexible packaging. The flexible packaging positions the two audio transducers so that they are respectively positioned over the ears of an infant. The device also includes a microphone device and electronics. The electronics receives signals from the microphone device, electronically filters the signals to attenuate frequencies above the range of a typical human voice, and provides the filtered electrical signals to the transducers to generate audio for the infant.

The electronics can also generate, from a recording, recorded electrical signals for playback to the infant. These recordings may be of family members' voices or the internal sounds of the mother's body, such as the mother's heartbeat.

In some implementations, the electronics attenuates frequencies above a cutoff frequency that is at least octave above a fundamental frequency of a typical human voice. One example cutoff frequency is in the range of 500 Hz.

In another example implementation, a server system can receive recordings from family members and associate the recording with an account created for the infant. These recordings may then transmitted to the medical device and be periodically played back to the infant during the infant's stay in the NICU. Such aural stimulation not only assists in development during the infant's stay in the NICU, but also familiarizes the infant to the voice(s) of the family member (s).

In some implementations, the audio level output of the transducers is at a level that is sufficiently low so as to ensure that hearing damage cannot occur from prolonged exposure. For example, the output level may be limited to 45 dB.

In some implementations, the electronics include an error detection circuit that monitors the audio output to ensure the audio output is being attenuated above the cutoff frequency. The error detection circuit may also monitor the output level to ensure the audio level is at or below a maximum output level. Should the error detection circuit detect that the audio is not being processed according to one or more output specifications, an error signal is generated and one or more remediation actions can be initiated.

These features and additional features are described in more detail below.

Example Aural Development Medical Device

FIG. 1 is an image of an infant 10 wearing an aural development medical device 100. As depicted in FIG. 1, speaker muffs 101 and 103 are worn against the infant's 10 ears. As shown in FIG. 1, the speaker muffs 101 and 103 are supra-aural headphones. In other implementations, circumaural headphones can be used. Other devices that can cover the ears or fit into the ears can also be used.

Figure 2:
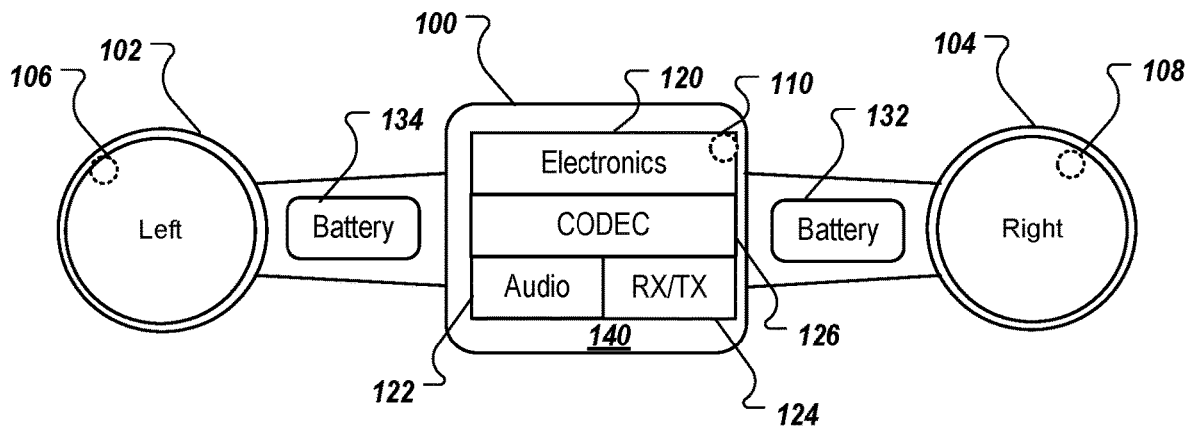
FIG. 2 is a diagram of an example implementation of the aural development medical device.

An example implementation of an aural development medical device 100 is illustrated in FIG. 2. As will be describe in more detail below, the device 100 is attached to a beanie 12 in a manner that allows the device 100 to be secured in place on the infant's 10 head while in a NICU incubator.

As shown in more detail in FIG. 2, the device 100 includes speakers 102 and 104 and at least one microphone. The speakers 102 and 104 are first and second audio transducer devices that each transduce electrical signals into acoustic sounds.

In some implementations, a microphone may be part of the speaker assembly, as shown in phantom by microphone 106 and 108. The microphone is a device that transduces received acoustic sounds into electrical input signals. The microphones may be placed on the outside of the speaker assemblies, and opposite the activation surfaces of the speakers 102 and 104. In another implementation, a single microphone may be used, such as the microphone 110. The placement of the single microphone 110 may be anywhere on the device 100, so long as the placement allows for the microphone 110 to detect sounds within the surrounding environment.

The speaker assemblies 102 and 104 may be enclosed in a padded, hypoallergenic housing to form the speaker muffs 101 and 103. The speaker muffs 101 and 103 offer a level of passive sound attenuation of noises from the surrounding environment that will protect the patient's hearing. In some implementations, the housings may be removed after a patient is discharged, and replaced with new housings after the device 100 is cleaned and sanitized.

The device 100 also includes electronics 120. The electronics 120 are electrically coupled to the first audio transducer device 102, the second audio transducer device 104, and the microphone device. As will be described in more detail below, the electronics 120 include an audio processing subsystem 122. The audio processing subsystem 122 receives the electrical input signals from the one or more microphone devices and electronically filters the electrical input signals to attenuate frequencies above a cutoff frequency $f_c$ and produce filtered electrical signals. The filtered electrical signals are then provided to the first audio transducer device 102 and the second audio transducer device 104.

In implementations where microphones 106 and 108 are used, the filtered electrical signals generated from the processing of the microphone 106 are provided to the speaker 102, and the filtered electrical signals generated from the processing of the microphone 108 are provided to the speaker 104. In other implementations that use only one microphone, such as microphone 110, the same filtered electrical signals are provided to both speakers 102 and 104.

The electronics 120 also include a transceiver subsystem 124 that can communicate with other systems wirelessly. Any appropriate transceiver system can be used, such as one that operates according to personal area network protocol, or one that operates according to a wireless area network protocol, or combinations thereof, or even other protocols.

The electronics 120 can associate the aural developmental medical device 100 with an identifier. For example, the identifier can be the MAC address of a radio device in the transceiver subsystem 124, or can be a unique identifier assigned to the device 100 and stored in a read only memory. Other identifiers, such as serial numbers, etc., can also be used. As will be described in more detail below, the device 100 identifier can be used to associate the device 100 with a patient identifier of a patient to which the device 100 is issued.

In one example implementation, the device 100 utilizes a Message Queuing Telemetry Transport (MATT) protocol for communication to receive a URI from which the audio may be streamed. In operation, the device 100, via the transceiver subsystem 124, receives a URI, e.g., a URL, that is a network address from which audio data may be retrieved. In some implementations, the URI may be used to establish an audio stream. In other implementations, the URI may be used to retrieve the audio data, store it locally in a memory of the device 100, and then process the audio data for playback.

The audio data may be processed by use of a CODEC 126. The type of CODEC used will depend on the format of the compressed audio data.

In an example implementation utilizing the MQTT protocol, the transceiver subsystem 124 utilizes an ESP8266 NodeMCU module. Other transceiver electronics and protocols can also be used, however.

The transceiver subsystem 124 can transmit and receive data over a network. In some implementations, the transceiver system 124 receives audio data encoding a recording and provides the data to the CODEC 126 for processing. The processed audio data is then provided to the audio subsystem 122. The audio subsystem 122 then generates, from the audio recording, recorded electrical signals and provides the recorded electrical signals to the first and second audio transducer devices 102 and 104. In this way recordings of family members, such as parents, may be played back to the patient.

Although shown as a component separate from the audio subsystem 122, the CODEC 126 can, of course, be a component of the audio subsystem 122.

In some implementations, the device 100 includes a memory storage that may store the audio data locally on the device 100 for periodic playback. After a patient to which the device 100 has been issued is discharged, the memory storage is overwritten via an automated discharge process. In another implementation, the memory storage may be a small removable storage device, such as a SIMM card, and the device may be removed upon discharge and provided to the parent(s) or caregiver(s) of the patient, or erased, or destroyed.

In other implementations, audio data is not stored on the device, and instead is received through the transceiver system as an audio stream. The CODEC 126 and the audio subsystem 122 then generate, from the audio stream, the recorded electrical signals and provide the recorded electrical signals to the first and second audio transducer devices 102 and 104.

The device 100 includes one or more batteries 132 and 134 to power the electronics 120 and the speakers 102 and 104. Although shown between the speakers 102 and 104 and the electronics 120, the one or more batteries 132 and 134 may be positioned elsewhere on the device 100.

The speakers 102, 104, microphone(s) 106, 108 and 110, electronics 120 and batteries 132 and 134 are contained within, mounted on or attached to a flexible packaging 140. As shown in FIGS. 1 and 2, the flexible packaging 140 positions the first and second audio transducer devices 102 and 104 relative to each other so that the first and second audio transducer devices 102 and 104 can be respectively positioned over a left ear and a right ear of an infant.

Other modules and subsystems may be included in the electronics 120, such as a controller, a memory, LED indicators, etc.

Figure 3A:
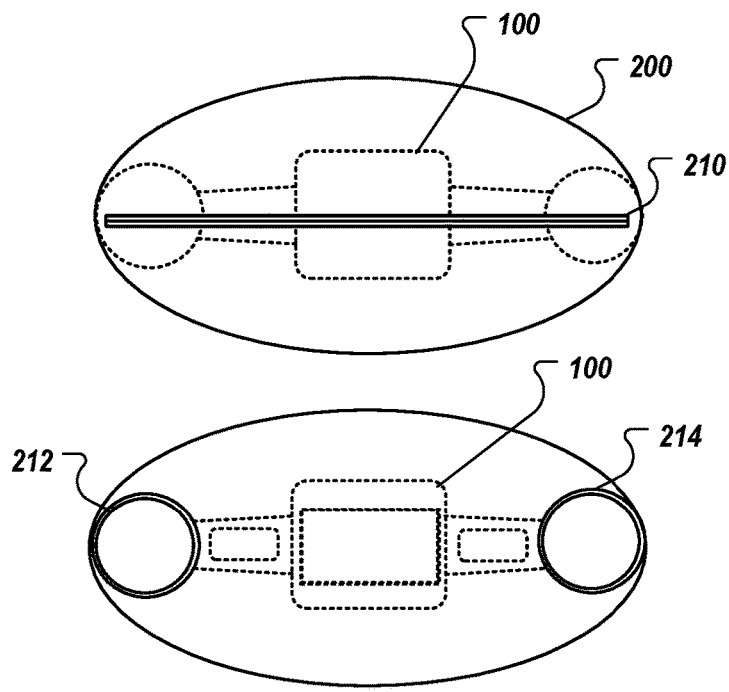
FIG. 3A is a diagram of an attachable packaging that houses the aural development medical device.

FIG. 3A is a diagram of an attachable packaging 200 that houses the aural development medical device 100. The attachable packaging 200 is in the form of a fabric pouch having an interior compartment fitted to secure the device 100. Additionally, the fabric pouch is attachable to headgear worn by an infant so that the speakers are respectively positioned over the right ear and the left ear of the infant when the headgear is worn by the infant.

The top and bottom portions of FIG. 3A show opposite sides of the attachable packaging. The portion of FIG. 3A shows a portion of the attachable packaging 200 that faces and attaches to the headgear worn by the infant. A fastening device 200, such as a zipper, is used to open the packaging and insert the device 100, and then to close the packaging 200 to secure the device 100 within the packaging 200. Other fasteners can also be used, such as hook and loop fastener, ties, buttons, etc.

The headgear to which the packaging may be attached can be a fabric beanie, for example. The attachable packaging 200 may be made of fabric that may be attached to the beanie, e.g., by use of a hook and loop fastener, or sewn on.

The bottom portion of FIG. 3A shows the portion of the packaging that comes contact with the patient's head. Opening 212 and 214 allow for speaker muffs 101 and 103 to protrude from the attachable packaging 200. As indicated by the phantom outline of the device 100, the attachable packaging 200 covers the electronics and flexible packaging 140 of the device 100. This precludes uncomfortable contact of the electronics and flexible packaging with the infant when the headgear is worn by the infant.

In other implementations, the fastener side may be on the same side of the packaging that comes in contact with the wearer's head.

The use of an attachable packaging 200 allows for removal of the device 100 from the headgear worn by the infant after the infant is discharged from the NICU. In other implementations, however, the headgear itself may include a pocket in which device 100 may be inserted. For example, beanie headgear may be manufactured with an inner fabric layer and an outer fabric layer, and the device 100 may be secured between the inner and outer fabric layers.

Figure 3B:
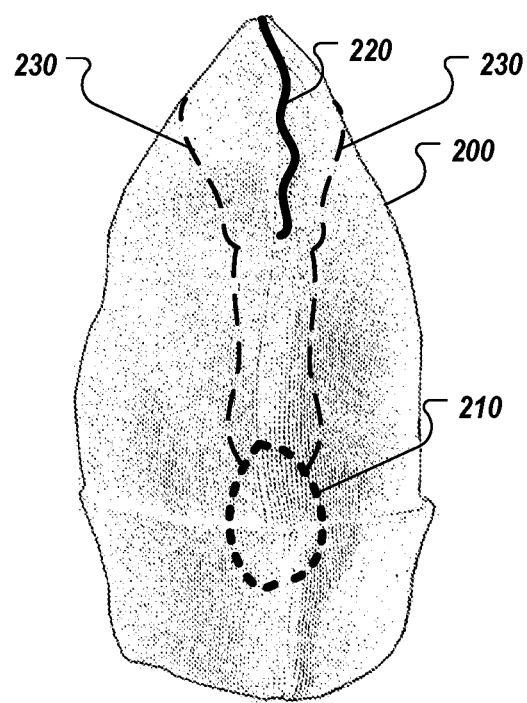
FIG. 3B is a diagram of a wearable headgear in which the aural development medical device may be directly inserted.

One example is illustrated in FIG. 3B, which is a diagram of a wearable headgear 200 in which the aural development medical device 100 may be directly inserted. The head gear has at least two fabric layers, and inner layer and an outer layer. The headgear 200 in FIG. 3B is depicted from a side to illustrate an opening 210, shown in phantom, in the inner layer through which a speaker muff will protrude when the device 100 is inserted between the inner and outer layers of the headgear 200. Another opening, not shown, is located in the inner layer on the other side of the headgear 200 to allow for protrusion of the other speaker muff of the device 100.

A fastener 200, such as a zipper or hook and loop fastener, is placed on the outer layer of the headgear 200 to allow for opening of the headgear 200 to insert or remove the device 100. As shown in FIG. 3B, the fastener is on the top of the outer layer of the headgear 200. In other implementations, an elastic opening, such as a slot, may be used, and the opening can be stretched to insert the device 100 into the headgear 200.

The inner and outer layers of the headgear 200 may be secured together along the phantom stitch line 230 to form an interior pocket that is shaped to receive the flexible packaging 140 of the device 100 so that when the fastener 220 is closed and the speaker muffs 101 and 103 protrude from the openings, the device 100 is held securely within the headgear 200. Thus, with the headgear 200 having the interior compartment fitted to secure device 100, the device does not contact the infant when the fabric beanie is worn by the infant.

Figure 4:
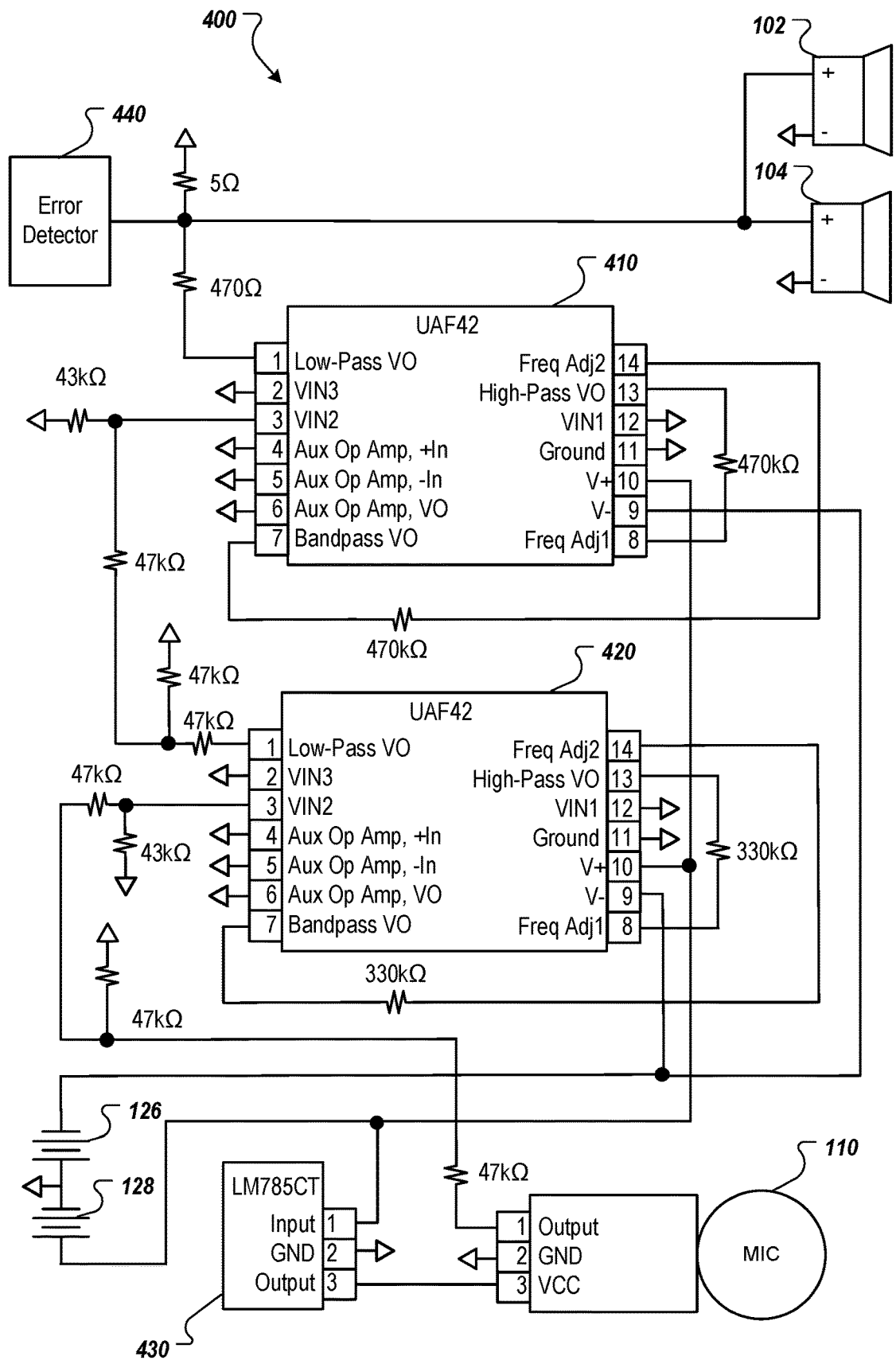
FIG. 4 is a circuit schematic a sound processing circuit of the aural development medical device.

FIG. 4 is a circuit schematic a sound processing circuit 400 of the aural development medical device 100. The sound processing circuit 400 may be part of the audio processing subsystem 122 of FIG. 2, and is responsible for active filtering of sound and limiting the output volume of the speaker 102 and 104. The sound processing circuit 400 is one example implementation that achieves the functions of active filtering and output level limiting. Other sound processing systems can also be used.

The sound processing circuit 400 includes a pair of active filters 410 and 420 that filter the output electrical signals provided to the speakers 102 and 104. In the example circuit 400 of FIG. 4, the active filters are UAF42 universal active filters. Batteries 132 and 134 provide power to circuit 400. A voltage regulator 430 is used to provide a drive voltage for the microphone 110.

In operation, acoustic waves detected by the microphone 110 are transduced into electrical input signals and provided to the active filter 410 as input. The active filter 410 is coupled to the active filter 420, and together the filters generate filtered electrical signals. These filtered electrical signals are then provided to the first audio transducer device 102 and the second audio transducer device 104, which, in turn, generate a filtered version of the sounds detected by the microphone 110.

The sound processing circuit 400 of FIG. 4 utilizes a single microphone to provide an audio signal for both speakers 102 and 104. In implementations in which each speaker 102 and 104 has a corresponding microphone to provide an audio signal, a similar sound processing circuit can be used for each speaker, but modified to drive only a single speaker for each microphone.

In some implementations, the circuit 400 includes an error detection circuit 440 that monitors the audio output to ensure the audio output is being attenuated above the cutoff frequency. For example, the signal that is provided to the speakers 102 and 104 can also be monitored through a high-impedance unity amplifier input to a spectral analysis circuit that processes the output electrical signals to determine attenuation across the frequency spectrum of interest, e.g., the range of human hearing. The error detection circuit 440 can thus monitor the output level of the audio to ensure the audio level is at or below a maximum output level. Should the circuit 440 determine that the attenuation above the cutoff frequency is not sufficient, e.g., the frequencies above the cutoff frequency are not attenuated at least a threshold amount relative to frequencies below the cutoff frequency, the circuit 440 can generate an error signal that is processed by a processing device in the electronics 120. Upon the occurrence of the error signal, the device 100 can send a notification to an external administration system, e.g., the system 610 of FIG. 6, to alert a health care provider of the error. The health care provider can then replace the device 100 with another device 100 and send the malfunctioning device to a provider for maintenance, repair or replacement.

The output level can also be monitored by the error detection circuit 440, and can generate an error signal if the output level is not within a threshold of a target output level, e.g., 45 dB±3 dB.

In some implementations, the error detection circuit 440 can also take precautionary actions on the device 100. For example, the circuit 440 may ground the output speakers 102 and 104 to preclude any noises from being generated by the speakers 102 and 104.

Figure 5:
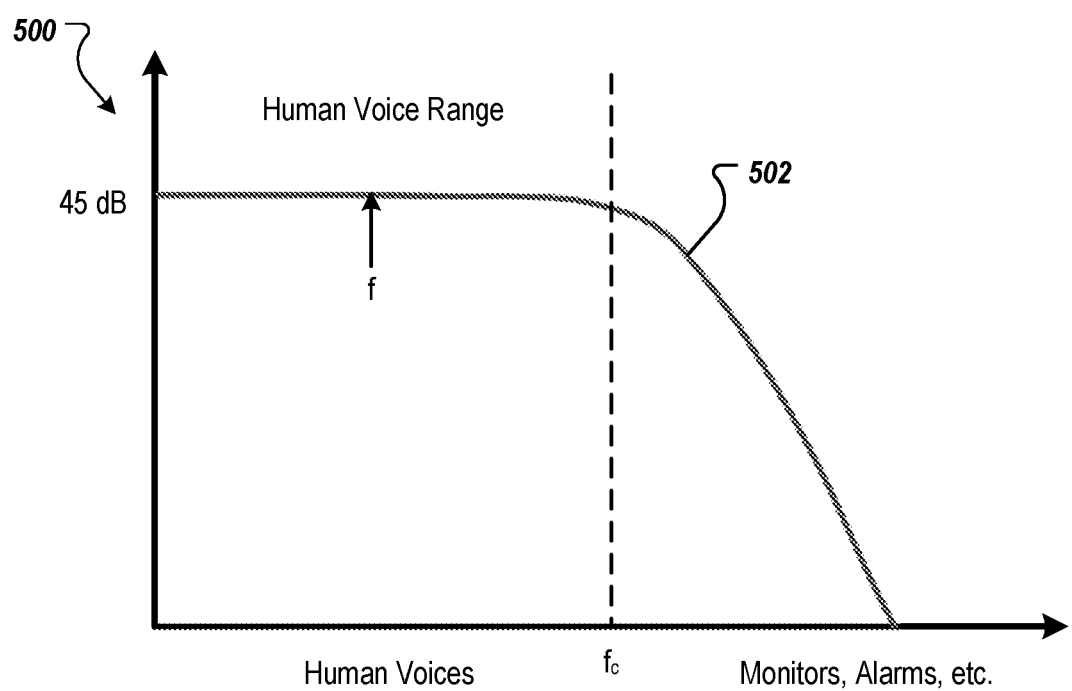
FIG. 5 is a graph of a frequency response of the sound processing circuit of FIG. 4.

FIG. 5 is a graph 500 of a frequency response 502 of the sound processing circuit 400 of FIG. 4. The cutoff frequency, in some implementations, is a frequency that is at least an octave above a fundamental frequency f of a typical human voice to generate filtered electrical signals. As shown in FIG. 4, the cutoff frequency f is approximately an octave above a fundamental frequency f of a human voice. For example, the typical fundamental frequency range of a human female voice is in the rage of 170 Hz to 255 Hz. Thus, in one implementation, the cutoff frequency is approximately 500 Hz. Accordingly, audio frequencies of most human voices are passed, while the audio frequencies of monitors, alarms, and other noises that are typically in excess of this cutoff frequency are attenuated.

The frequency response curve of FIG. 5 is illustrative, and other filter designs with different response curves can also be used.

In some implementations, the audio output level of the speakers 102 and 104 is limited to a sound level that is low enough to ensure that prolonged exposure to the audio will not damage the infants' hearing. In some implementations, this level is 45 dB. Other maximum levels can also be used, however, such as 50 dB or even higher. Likewise, a maximum level can also be less than 45 dB, e.g., 40 dB.

Example Aural Development Medical Device System

As described above, the device 100 attenuates noises and sounds that are above the normal frequency envelope of the human voice while passing frequencies that are within the normal frequency envelope of the human voice. Moreover, the output level of the speakers is limited so that unfiltered sounds, e.g., the sounds of human voices, detected from the microphone(s) are output at safe levels.

Also as described above, the device 100 may receive audio data encoding a recording and play back the recording on the speakers 102 and 104. Again, the audio levels of playback may be limited to the safe audio level. Moreover, during playback, in some implementations, audio detected from the microphone(s) is not processed, and thus the electronics do not provide electrical signal generated in response to an electrical input signal generated by the microphone device during playback. This enables the infant to focus on the sounds of the recordings by reducing distractions that extraneous voices and noises might otherwise cause.

Parents and caregivers of NICU patients, however, are often not able to be with infants during the NICU stay. Accordingly, an aural development management system allows for the parents and caregivers to provide audio recordings of their voices that can be played back to the infants.

Figure 6:
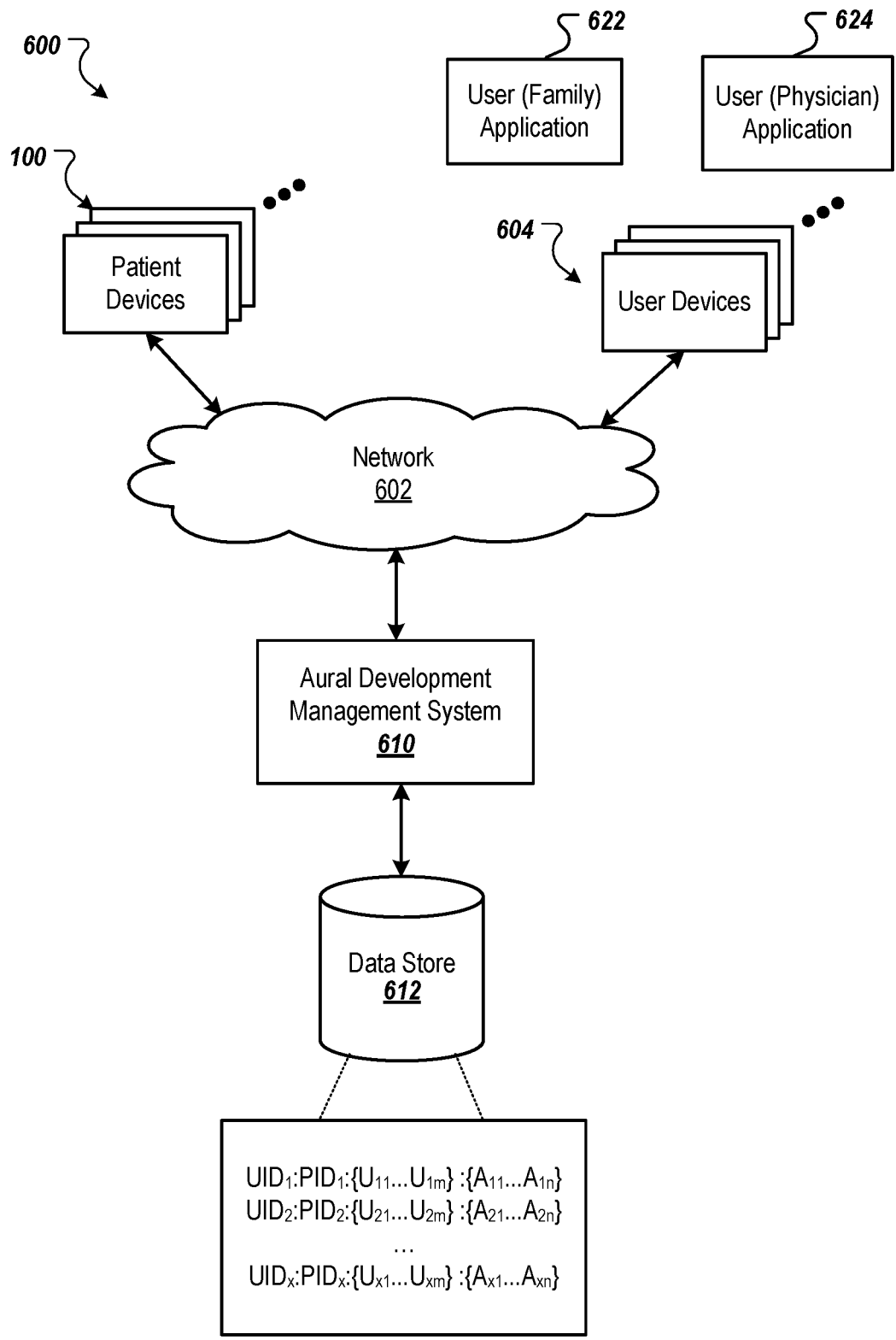
FIG. 6 is a block diagram of an aural development medical device system.

FIG. 6 is a block diagram of an example aural development medical device system 600. The system includes patient devices 100, such as the device 100 of FIG. 2, in data communication over a network 602 with an aural development management system 610. The network 602 may be a computer, such as a local area network (LAN), wide area network (WAN), the Internet, or a combination thereof. More generally, any protocol that is appropriate for transmitting recorded audio can be used in the network 602.

The aural development management system 610 may be realized by one or more computers in data communication with each other and running an application(s) that perform the operations described below, or programmed to perform the operations described below.

The system also includes one or more applications, such as user (family) applications 622 and user (physician) applications 624 that each run on user devices 604. The user devices 604 may be, for example, smart phones or computers. Through a family application 622, a user may record his or her voice and upload the recording for later playback to a particular patient device 100. The family application 622 may also allow for the deletion of certain recordings, and for the scheduling of playback of the recordings.

The physician application 624 may include the same functionalities of the family application 622, and may also include other functionalities that are reserved for physicians, physician assistants, nurses, and other hospital staff. These functionalities may include overriding or adjusting playback schedules set by users of the family application 622, setting cumulative playback time for a time period, and associating and de-associating a particular device 100 with a particular patient.

In operation of the system 600, each device 100 is issued to a patient and has a corresponding unique identifier UID. The device may be a MAC address, or an address stored in a memory on the device 100. Upon issuance, the unique identifier UID is associated with a patient identifier PID. The PID may be a hospital patient identifier for the patient.

In some implementations, each UID is a permanent identifier assigned to a particular user device. In other implementations, the UID may be temporarily stored on the device 100 in a memory, and may, for example, be the patient identifier PID. Each particular device 100 may be accessed based on the UID of the device 100.

For each patient, one or more user identifiers U are associated with the patient identifier of the patient. This may be done by setting up an account through the physician application 624, or by setting up the account after downloading and launching a family application to a user device 604. For example, once a device 100 with a user identifier UID is issued to a patient with a patient identifier PID, the UID and PID are associated with each other. Thereafter, a unique uniform resource identifier (URI) link may be generated and sent to a family member listed as a caregiver of the patient. The family member may download the family application 622 by selecting the link on the user device 604, and then proceed to set up an account on the aural development management system 610. The account is linked to corresponding identifiers. During this time, the family member may add additional users to the account, should the family member choose to do so.

The users that are associated with a patient identifier in an account are authorized to provide audio data encoding recordings for presentation on the aural developmental medical device 100 issued to the patient. This can be done, for example, by a particular user recording the audio files by use of the family application 622. Once recorded, the audio file is transmitted from the user device 622 to the system 610 via the network 602. Based on the particular user as identified by the user identifier, the system 610 determines the particular patient associated with the particular user. After the particular patient is determined, the system 610 stores in a data store 610, in association with the particular patient, the audio data encoding the recording and received from the user device.

Thus, for each particular device 100, the following data set is established:

$$UID_x:PID_x:\{U_{x1} \ldots U_{xm}\}:\{A_{x1} \ldots A_{xn}\}$$

where:
$UID_x$ is the unique identifier of the device 100;
$PID_x$ is the patient identifier of the particular patient;
$\{U_{x1} \ldots U_{xm}\}$ are the users associated with the particular patient identifier; and
$\{A_{x1} \ldots A_{xn}\}$ are the audio files recorded by the users associated with the particular patient identifier.

The audio files are stored in the data store 612 and are addressed by and accessible by use of the URI provided by the system 610 to the corresponding user devices 100. In some implementations, the audio files may be of any playback length, and need not be of a fixed duration or size.

In implementation in which the devices 100 have local memory to store the audio files, the system 610 sends, to the aural developmental medical device 100 issued to the particular patient, the audio data encoding the recordings. The data may also include a playback schedule, and the device 100 then processes the audio files to generate recorded electrical signals and provide the recorded electrical signals to the first and second audio transducer devices according to the playback schedule.

In other implementations in which the devices 100 does not store audio files, the system 610 stores the playback schedule and streams the audio data to the device 100 for processing according to the playback schedule.

The audio files typically record human voices, such as the voices of the mother and other family members. Other recordings can also be recordings of an internal sound of a human body, such as a recording of the sounds of the mother's body. In some implementations, the recordings of the sounds of the mother's body may be played back constantly between the playback of other recordings. Given that each patient is recently born, the familiar internal sounds of the mother's body will tend to calm and comfort the patient. In variations of this implementation, the body sounds may be overlaid with the mother's voice, or recorded while the mother is speaking.

In some implementations, upon recording on a user device 604, or when being stored by the system 610, the audio data is filtered to attenuate frequencies that are above the cutoff frequency $f_c$. Accordingly, when the audio is processed by the user device 100, filtering of the audio need not be performed on the device 100. This can be done, for example, to conserve battery power. In other implementations, the decompressed audio is filtered by the filtering circuit to ensure that frequencies above the cutoff frequency $f_c$ are attenuated.

Figure 7:
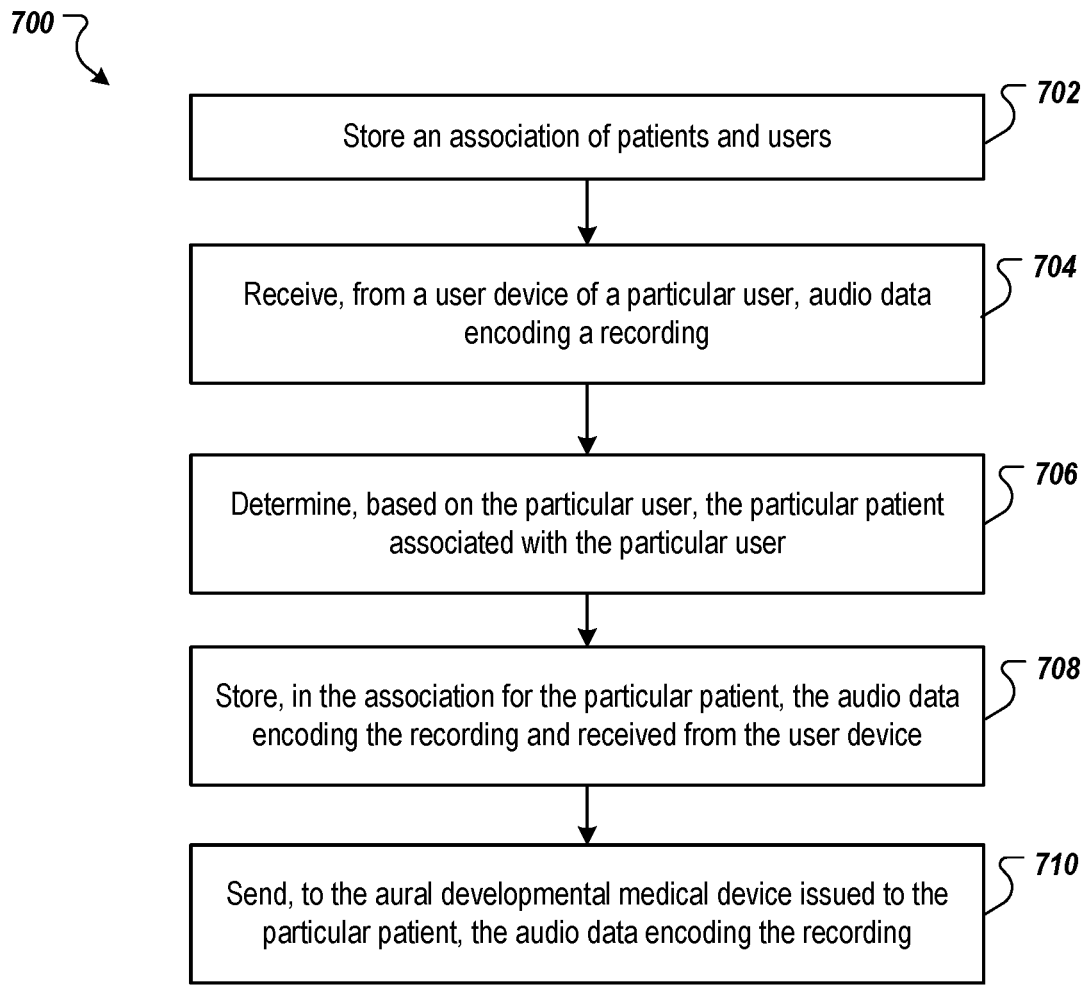
FIG. 7 is a flow diagram of an example process for storing and providing audio data in the system of FIG. 6.

FIG. 7 is a flow diagram of an example process 700 for storing and providing audio data in the system 600 of FIG. 6. The process 700 can be implemented on a computer system of one or more computers.

The process 700 stores an association of patients and users (702). For example, one or more users, by use of the family application 622 or the physician application 624, are assigned user identifiers that are associated with a patient identifier of a patient. This association is stored in the data store 612 by the system 610.

The process 700 receives, from a user device of a particular user, audio data encoding a recording (704). For example, a user may launch the family application 622, input his or her identifier, and then record his or her voice to be played back to the patient. This recording is encoded audio data and sent to the system 610.

The process 700 determines, based on the particular user, the particular patient associated with the particular user (706). For example, the audio recording is paired with the user identifier of the user using the application 622, and is sent to the system 610. Based on the association of user identifiers and patient identifiers, the particular patient is determined by the system 610.

The process 700 stores, in the association for the particular patient, the audio data encoding the recording and received from the user device (708). For example, the system 610 stores the audio data in associate with particular patient in the data store 612.

The process 700 sends, to the aural developmental medical device issued to the particular patient, the audio data encoding the recording (710). For example, the system 610 may send the audio data to the patient device 100 for storage on the device 100 if the device has local storage for storing audio files. Otherwise, the system 610 may send the audio data to the patient device 100 via a stream during playback of the audio data.

Figure 8:
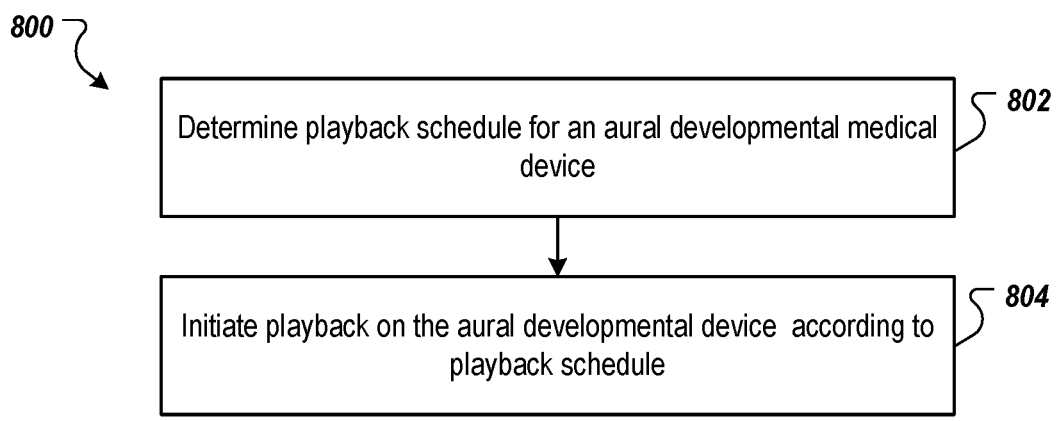
FIG. 8 is a flow diagram of an example process for managing a playback schedule for a particular aural development medical device.

FIG. 8 is a flow diagram of an example process 800 for managing a playback schedule for a particular aural development medical device. The process 800 can be implemented on a computer system of one or more computers.

The process 800 determines a playback schedule for an aural developmental medical device (802). For example, the audio files associated with a particular patient may each have a respective playback time or playback event. Unlike a playback time, and playback event is not time dependent, but is dependent on the occurrence of an event that is performed. In the case of the latter, a playback event may be, for example, the conclusion of a feeding.

The process 800 initiates playback on the aural developmental device according to playback schedule (804). For example, if the playback schedule is time based, an audio file for a particular device is streamed to the device at the time specified in the playback schedule. Conversely, if the playback schedule is event based, the audio file is streamed upon the occurrence of the event. The system 610 may determine the event has occurred when hospital staff updates a patient chart with data indicating the event occurred. For example, at the conclusion of feeding, a nurse may update a patient's chart to indicate that the patient has been fed. The system 610 may be linked to the patient chart and upon receiving the update will determine the event has occurred and stream scheduled audio file. More generally, the system 610 may interface with a caregiver system, e.g., a hospital system, via an API or some other software solution, and may be programmed to determine that the occurrence of certain activities that are recorded in the system as being completed, e.g., feeding, changing, etc., as events.

Additional Implementation Details

In situations in which the systems discussed here collect personal information about users, or may make use of personal information, the users may be provided with an opportunity to control whether applications or features collect user information (e.g., information about a user's social network, social actions or activities, profession, a user's preferences, or a user's current location), or to control whether and/or how to receive content that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a user computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any features or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. An aural developmental medical device, comprising:
   a first audio transducer device and a second audio transducer device that each transduce electrical signals into acoustic sounds;
   at least one microphone device that transduces received acoustic sounds into electrical input signals;
   electronics electrically coupled to the first audio transducer device, the second audio transducer device, and the at least one microphone device, wherein the electronics are operable to:
      associate the aural developmental medical device with an identifier, wherein the identifier is an aural medial development device identifier and is associated with a patient identifier of a patient to which the aural medial development device is assigned; and
      receive the electrical input signals from the at least one microphone device;
      electronically filter the electrical input signals to attenuate frequencies above a cutoff frequency that is at least octave above a fundamental frequency of a typical human voice to generate filtered electrical signals;
      provide the filtered electrical signals to the first audio transducer device and the second audio transducer device;
      receive audio data encoding a recording based on the association of the patient identifier and the aural medial development device identifier;
      generate recorded electrical signals from the audio data encoding the recording and associated with the identifier; and
      provide the recorded electrical signals to the first audio transducer device and the second audio transducer device; and
   a flexible packaging that positions the first and second audio transducer devices relative to each other so that the first and second audio transducer devices can be respectively positioned over a left ear and a right ear of an infant.

2. The aural developmental medical device of claim 1, wherein the cutoff frequency is approximately 500 Hz.

3. An aural developmental medical device, comprising:
   a first audio transducer device and a second audio transducer device that each transduce electrical signals into acoustic sounds;
   at least one microphone device that transduces received acoustic sounds into electrical input signals;
   electronics electrically coupled to the first audio transducer device, the second audio transducer device, and the at least one microphone device, wherein the electronics are operable to:
      associate the aural developmental medical device with an identifier; and
      receive the electrical input signals from the at least one microphone device;
      electronically filter the electrical input signals to attenuate frequencies above a cutoff frequency that is at least octave above a fundamental frequency of a typical human voice to generate filtered electrical signals;
      provide the filtered electrical signals to the first audio transducer device and the second audio transducer device;
      generate recorded electrical signals from audio data encoding a recording and associated with the identifier; and
      provide the recorded electrical signals to the first audio transducer device and the second audio transducer device; and
   a flexible packaging that positions the first and second audio transducer devices relative to each other so that the first and second audio transducer devices can be respectively positioned over a left ear and a right ear of an infant;
   wherein the flexible packaging comprises a fabric beanie, wherein:
   the fabric beaning comprises an interior compartment fitted to secure the first and second audio transducers devices, the at least one microphone device, and the electronics so that at least the at least one microphone device and the electronics are within the interior compartment and do not contact the infant when the fabric beanie is worn by the infant.

4. An aural developmental medical device, comprising:
   a first audio transducer device and a second audio transducer device that each transduce electrical signals into acoustic sounds;
   at least one microphone device that transduces received acoustic sounds into electrical input signals;
   electronics electrically coupled to the first audio transducer device, the second audio transducer device, and the at least one microphone device, wherein the electronics are operable to:
      associate the aural developmental medical device with an identifier; and
      receive the electrical input signals from the at least one microphone device;
      electronically filter the electrical input signals to attenuate frequencies above a cutoff frequency that is at least octave above a fundamental frequency of a typical human voice to generate filtered electrical signals;
      provide the filtered electrical signals to the first audio transducer device and the second audio transducer device;

generate recorded electrical signals from audio data encoding a recording and associated with the identifier; and provide the recorded electrical signals to the first audio transducer device and the second audio transducer device; and a flexible packaging that positions the first and second audio transducer devices relative to each other so that the first and second audio transducer devices can be respectively positioned over a left ear and a right ear of an infant;

wherein the flexible packaging comprises a fabric pouch, wherein:

the fabric pouches comprises an interior compartment fitted to secure the first and second audio transducers devices, the at least one microphone device, and the electronics so that at least the at least one microphone device and the electronics are within the interior compartment;

the fabric pouch is attachable to headgear that is worn by an infant so that the first and second audio transducer devices are respectively positioned over the right ear and the left ear of the infant when the headgear is worn by the infant; and the at least the at least one microphone device and the electronics within the interior compartment do not contact the infant when the headgear is worn by the infant.

5. The aural developmental medical device of claim 1, wherein:

the electronics comprises a transceiver subsystem, and wherein the electronics are further operable to receive, over the transceiver subsystem, the audio data encoding the recording based on the association of the patient identifier and the aural medial development device identifier.

6. The aural developmental medical device of claim 5, wherein the recording is a recording of a human voice.

7. The aural developmental medical device of claim 6, wherein the electronics are further operable to:

store the audio data encoding the recording of the human voice; and periodically generate, from audio data encoding a recording of a human voice, the recorded electrical signals and provide the recorded electrical signals to the first audio transducer device and the second audio transducer device according to a playback schedule a plurality of different times according to the playback schedule.

8. The aural developmental medical device of claim 6, wherein the electronics are further operable to:

receive, over the transceiver system, a notification to generate and provide recorded electrical signals to the first and second audio transducer devices, and in response:

receive, over the transceiver system, the audio data encoding a recording of a human voice as an audio stream; and generate, from the audio stream, the recorded electrical signals and provide the recorded electrical signals to the first audio transducer device and the second audio transducer device according to a playback schedule.

9. The aural development medical device of claim 1, wherein the electronics are further configured to:

not provide electrical signal generated in response to electrical input signal generated by the at least one microphone device when providing the recorded electrical signals to the first audio transducer device and the second audio transducer device.

10. The aural development medical device of claim 1, wherein the electronics are further configured to limit recorded electrical signals and the filtered electrical signals to a magnitude the limit a sound level of the acoustic sounds generated by the first and second transducers to approximately 45 db.

11. The aural developmental medical device of claim 1, wherein the recording is a recording of an internal sound of a human body.

12. An aural developmental medical device, comprising:

a first audio transducer device and a second audio transducer device that each transduce electrical signals into acoustic sounds;

at least one microphone device that transduces received acoustic sounds into electrical input signals;

electronics electrically coupled to the first audio transducer device, the second audio transducer device, and the at least one microphone device, wherein the electronics are operable to:

associate the aural developmental medical device with an identifier; and receive the electrical input signals from the at least one microphone device;

electronically filter the electrical input signals to attenuate frequencies above a cutoff frequency that is at least octave above a fundamental frequency of a typical human voice to generate filtered electrical signals;

provide the filtered electrical signals to the first audio transducer device and the second audio transducer device;

generate recorded electrical signals from audio data encoding a recording and associated with the identifier; and provide the recorded electrical signals to the first audio transducer device and the second audio transducer device;

a flexible packaging that positions the first and second audio transducer devices relative to each other so that the first and second audio transducer devices can be respectively positioned over a left ear and a right ear of an infant; and an error detection device that monitors the frequency spectrum of the filtered electrical signals and generates an error signal when the monitoring of the frequency spectrum of the filtered electrical signals indicates frequencies above the cutoff frequency are not attenuated at least a threshold amount relative to frequencies below the cutoff frequency.

13. A system, comprising:

one or more computer devices; and instructions stored in a non-transitory computer readable medium that are executable by the one or more computer devices, and upon such execution cause the one or more computer devices to perform operations comprising:

storing an association of patients and users, wherein the association establishes, for each patient:

an aural developmental medical device issued to the patient and identified by a unique identifier;

one or more users that are authorized to provide audio data for recording and later presentation on the aural developmental medical device issued to the patient;

receiving, over a computer network and from a user device that is remote from the one or more computer devices and associated with a particular user, audio data encoding a recording;

receiving, over the computer network, playback schedule data associated with the audio data encoding the recording, the playback schedule data defining a playback schedule that causes an aural developmental medical device issued to the particular patient to process the audio data encoding the recording periodically according to the playback schedule to periodically present the recording, wherein the recording is presented a plurality of different times according to the playback schedule;

determining, based on the particular user, the particular patient associated with the particular user;

storing, in the association for the particular patient:
the audio data encoding the recording and received from the user device; and
the playback schedule data associated with the audio data; and sending, to the aural developmental medical device issued to the particular patient, the audio data encoding the recording.

14. The system of claim 13, wherein the recording is of a human voice.

15. The system of claim 13, wherein sending, to the aural developmental medical device issued to the particular patient, the audio data encoding the recording comprises streaming, to the aural developmental medical device issued to the particular patient, the audio data encoding the recording according to the playback schedule defined by the playback schedule data associated with the audio data.

16. A method, comprising:
storing an association of patients and users, wherein the association establishes, for each patient:
an aural developmental medical device issued to the patient and identified by a unique identifier;
one or more users that are authorized to provide audio data for presentation on the aural developmental medical device issued to the patient;
receiving, over a computer network and from a user device that is remote from the one or more computer devices and associated with a particular user, audio data encoding a recording;
receiving, over the computer network, playback schedule data associated with the audio data encoding the recording, the playback schedule data defining a playback schedule that causes an aural developmental medical device issued to the particular patient to process the audio data encoding the recording periodically according to the playback schedule to periodically present the recording, wherein the recording is presented a plurality of different times according to the playback schedule;

determining, based on the particular user, the particular patient associated with the particular user;

storing, in the association for the particular patient:
the audio data encoding the recording and received from the user device; and
the playback schedule data associated with the audio data; and sending, to the aural developmental medical device issued to the particular patient, the audio data encoding the recording.

17. The method of claim 16, wherein the recording is of a human voice.

18. The method of claim 16, further comprising:
determining, for the particular patient, a playback schedule; and
sending, to the aural developmental medical device issued to the particular patient, the audio data encoding the recording, according to the playback schedule.

19. The method of claim 16, wherein sending, to the aural developmental medical device issued to the particular patient, the audio data encoding the recording comprises streaming, to the aural developmental medical device issued to the particular patient, the audio data encoding the recording according to the playback schedule.

20. The system of claim 13, wherein:
sending, to the aural developmental medical device issued to the particular patient, the audio data encoding the recording further comprises sending, the to the aural developmental medical device issued to the particular patient, the playback schedule data associated with the audio data encoding the recording; and
the aural developmental medical device is configured to store the audio data encoding the recording and the playback schedule data and process the audio data periodically according to the playback schedule to periodically present the recording.

* * * * *